United States Patent [19]

Burt et al.

[11] Patent Number: 5,464,442
[45] Date of Patent: Nov. 7, 1995

[54] TUBULAR SUPPORT PYLON AND RETAINER FOR PROSTHETIC FOOT

[75] Inventors: Edward W. Burt, Bellevue; William E. Bryant, Everett; David M. Crist, Seattle, all of Wash.

[73] Assignee: Model & Instrument Development Corporation, Seattle, Wash.

[21] Appl. No.: 90,608

[22] Filed: Jul. 12, 1993

[51] Int. Cl.⁶ ............................................. A61F 2/60
[52] U.S. Cl. ............................... 623/27; 267/140.13
[58] Field of Search ................ 623/27; 138/DIG. 2, 138/DIG. 7; 464/183; 267/140.11, 140.13

[56] References Cited

U.S. PATENT DOCUMENTS

| | | | |
|---|---|---|---|
| 3,691,000 | 9/1972 | Kalnin | 138/DIG. 2 X |
| 3,893,196 | 7/1975 | Hochman | 606/76 X |
| 4,005,858 | 2/1977 | Lochner | 267/140.13 X |
| 4,104,095 | 8/1978 | Shaw | 138/DIG. 2 X |
| 4,186,696 | 2/1980 | Linsenmann | 464/183 X |
| 4,311,406 | 1/1982 | Driver | 403/161 |
| 4,397,048 | 8/1983 | Brown et al. | 623/27 |
| 4,421,202 | 12/1983 | Hoy | 138/DIG. 2 X |
| 4,822,363 | 4/1989 | Phillips | 623/27 |
| 4,863,416 | 9/1989 | Gupta | 464/181 |
| 4,938,776 | 7/1990 | Masinter | 623/49 |
| 5,219,364 | 6/1993 | Lloyd | 623/33 |

OTHER PUBLICATIONS

Quigley, "Prosthetic Methods and Materials", in *Atlas of Limb Prosthetics: Surgical and Prosthetic Principles*, Mosby: St. Louis (1981), pp. 58–62.

*Primary Examiner*—David H. Willse
*Attorney, Agent, or Firm*—Seed and Berry

[57] ABSTRACT

A prosthetic support pylon is disclosed that is comprised of a tubular inner member being deformable along its longitudinal axis and comprised of a material having a composite stiffness value of between about 30,000 pounds·inch$^2$ and about 200,000 pounds·inch$^2$ and a tubular outer member over the tubular inner portion. The tubular outer member is comprised of a dampening material which slows the release of the energy produced by the tubular inner member upon return from deformation along its longitudinal axis. The material of the tubular inner member is comprised of a support matrix and of stiffening fibers which are most preferably selected from a group consisting of carbon, graphite, fiberglass, ultra high molecular weight polyethylene and aramid. The support matrix of the tubular inner member is most preferably selected from the group consisting of epoxy, vinyl ester and polyester. The tubular outer member is comprised of a thermoplastic material most preferably selected from a group consisting of polyamide, acetal, aromatic polyester, and polysulfone. A retainer holds an end of the prosthetic support pylon therein, and the axial rotation of the pylon is minimized by a screw on the retainer exterior which has threads that bite into the pylon through a slot in the retainer.

15 Claims, 5 Drawing Sheets

TUBULAR SUPPORT PYLON AND RETAINER FOR PROSTHETIC FOOT

BACKGROUND OF THE INVENTION

The invention pertains to limb prosthesis, and more specifically to a lower leg member for extending an amputee's shortened limb and for connecting at the lower end to a prosthetic foot. Prosthetic pylons must be strong enough to support the body weight of the person while providing the proper combination of stiffness, flexation and damping to simulate the natural human stride. More specifically, the requisite degree of stiffness in a pylon is required to return energy back to the stride of the wearer at "toe-off". Sufficient damping must be present in the pylon to absorb the shock that occurs at "heel strike" when the pylon is returning from deformation, primarily bending, along its longitudinal axis.

Support pylons comprised of stiffening fibers in a polymeric binding matrix are generally known. Known prior art pylons are generally solid members having the stiffening fibers located either on the exterior surface of, or interspersed homogeneously throughout, the pylon. Solid pylons having larger cross-sections are too stiff to simulate the natural human stride, while solid pylons having lesser cross-sections provide inadequate damping and are not compatible with the prosthetic foot clamps generally in use. Furthermore, in pylons having either stiffening fibers homogeneously dispersed therein or pylons having an exterior layer of stiffening fibers, the resulting overall stiffness of the pylons is not optimum. Stiffening fibers located at or near the exterior of the pylon tended to become ineffective after a short period of use because of repeated bending stress at the exterior of the pylon which is greater than the strain tolerance of the fibers. The above is true for substantially all of the fibers in the pylons having stiffening fibers located on or proximate their exterior surfaces and is also the case for the majority of the fibers in pylons having stiffening fibers homogeneously dispersed.

SUMMARY OF THE INVENTION

The present invention provides a hollow prosthetic support pylon having the majority of stiffening fibers located nearer the longitudinal axis of the pylon such that the requisite composite stiffness and damping can be obtained to simulate the natural stride while maintaining adequate material strength to support the body weight, providing sufficient pylon circumference to fit known foot prosthesis clamps, and stiffening fibers configured to prevent premature fatigue due to repetitive bending during striding, all in a prosthesis that makes efficient use of the relatively expensive stiffening fibers employed in manufacture.

In a first embodiment, a prosthetic support pylon has a tubular inner member that is deformable along its longitudinal axis and is made of a material having a composite stiffness value of between about 30,000 pounds·inch$^2$ and about 200,000 pounds·inch$^2$ and a tubular outer member coaxial with and attached to the tubular inner member. The tubular outer member is comprised of a dampening material which slows the release of the spring back energy produced by the tubular inner member upon return from deformation along its longitudinal axis.

Preferably, the material forming the tubular inner member is comprised of a support matrix or binder and of stiffening fibers. Most preferably, the stiffening fibers are selected from a group consisting of carbon, graphite, fiberglass, ultra high molecular weight polyethylene and aramid. The stiffening fibers are most preferably carbon and are homogeneously distributed in the support matrix. The stiffening fibers are preferably oriented parallel with the longitudinal axis of the tubular inner member. An alternative embodiment has fibers oriented at different angles such as about 45° with respect to the longitudinal axis of the tubular inner member so that the stiffening fibers assume a helical configuration around the longitudinal axis interleaved in both clockwise and counterclockwise directions and reduces the bending stiffness thereof. Preferably, the stiffening fibers comprise about 60% by weight of the composite tubular inner member. The support matrix of the tubular inner member is preferably selected from the group consisting of thermoplastic and thermoset. The support matrix of the tubular inner member is most preferably selected from the group consisting of epoxy, vinyl ester and polyester. The tubular inner member may also be further comprised of a layer of fiberglass in an epoxy matrix on the exterior surface of the tubular inner member. Most preferably, the fiberglass is comprised of fibers oriented both parallel with and perpendicular to the longitudinal axis of the tubular inner member.

Preferably, the tubular outer member is comprised of a thermoplastic material. This thermoplastic material is most preferably selected from a group consisting of polyamide, acetal, aromatic polyester, and polysulfone. The prosthetic support pylon is preferably between about 9.50 inches and about 16.50 inches in length, the tubular inner member has an outside diameter (O.D.) of between about 0.640 inch and about 0.750 inch, and the tubular outer member has an inside diameter (I.D.) of between about 0.640 inch and about 0.750 inch and has an outside diameter of 1.181 inch.

In the second embodiment of the present invention, a prosthetic support pylon is comprised of a unitary tubular member being deformable along its longitudinal axis and having an inner portion and an outer portion. The inner portion has a composite stiffness value of between about 30,000 pounds·inch$^2$ and about 200,000 pounds·inch$^2$. The outer portion is comprised of a material which slows the release of the spring back energy produced by the inner portion of the unitary tubular member upon return from deformation along its longitudinal axis. Preferably, the inner portion and the outer portion of the prosthetic support pylon of the second embodiment are comprised of a thermoplastic or a thermoset. Most preferably, the inner portion and the outer portion are selected from the group consisting of polyamide, vinyl ester, and acetal. Additionally, the inner portion is further comprised of stiffening fibers selected from a group consisting of carbon, graphite, fiberglass, ultra high molecular weight polyethylene and aramid. The stiffening fibers may be oriented either parallel with the longitudinal axis of the inner portion, or at about 45° with respect to the longitudinal axis of the inner portion such that they are helically wound around the longitudinal axis of the inner portion in both clockwise and counterclockwise directions. Most preferably, the prosthetic support pylon of the second embodiment has a length of between about 10.00 inches and about 17.00 inches, the inner portion has an outside diameter (O.D.) of between about 0.640 inch and about 0.750 inch, and the outer portion has an inside diameter (I.D.) of between about 0.640 inch and about 0.750 inch.

The present invention also encompasses a retainer for use with the prosthetic support pylons of the above two embodiments, as well as with other prosthetic support pylons. The retainer includes a sleeve having a bottom and a wall forming an interior for retaining an end of the prosthetic support pylon therein. The sleeve has an opening in the wall.

The retainer also includes means for minimizing the axial rotation of the prosthetic support pylon relative to the sleeve that is located on the exterior of the sleeve wall and adjacent to the opening in the sleeve wall. In this configuration, the means for minimizing axial rotation contacts a portion of the prosthetic support pylon by protruding through the opening in the sleeve wall. Most preferably, the means for minimizing axial rotation is comprised of nuts on the exterior of the wall of the sleeve, these nuts being located adjacent to the opening in the sleeve wall. The means for minimizing axial rotation further comprises a screw adapted to fit the nuts such that the threads of the screw bite into a portion of the prosthetic support pylon by protruding through the opening in the sleeve wall. Most preferably, the nuts are axially rotatable between a first position where the screw protrudes through the opening in the sleeve wall, and a second position where the screw does not protrude through the opening in the sleeve wall such that the retainer can accommodate both a prosthetic support pylon comprised of a synthetic polymer when the nuts are oriented in the first position, and a prosthetic support pylon comprised of a metal alloy when the nuts are oriented in the second position.

BRIEF DESCRIPTION OF THE DRAWINGS

These and other features of the present invention will be more fully appreciated when considered in light of the following specification and drawings in which.

DETAILED DESCRIPTION OF THE PREFERRED EMBODIMENTS

Figure 1:
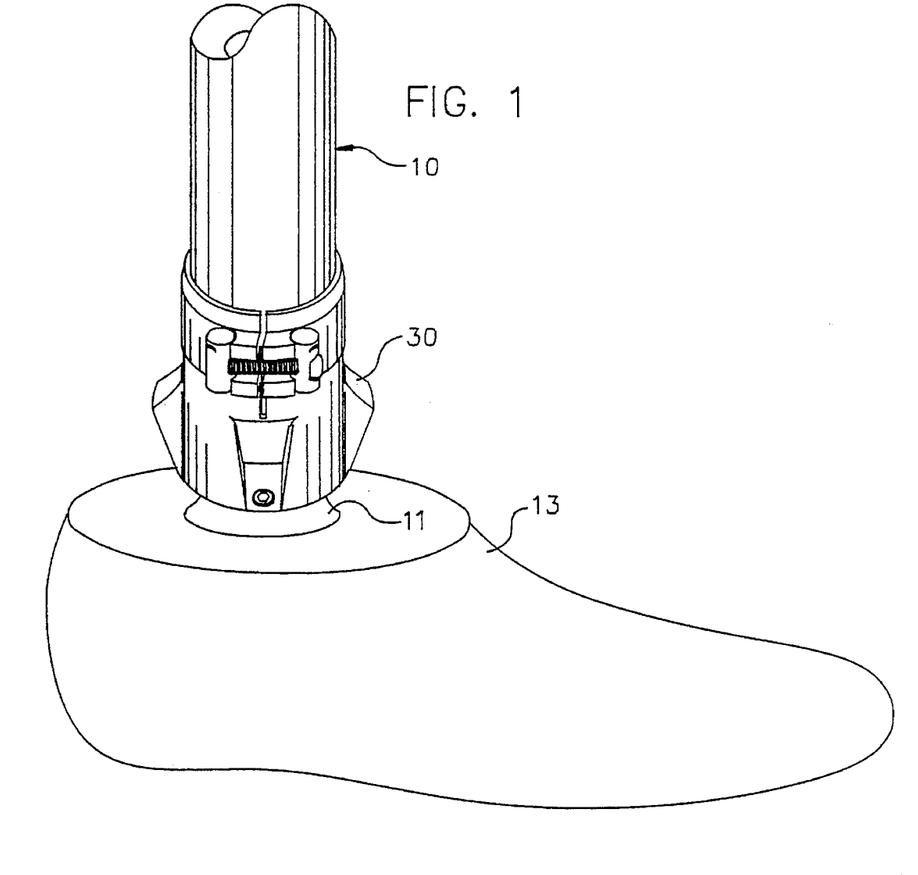
FIG. 1 is an isometric view of the prosthetic support pylon and retainer of the present invention.

Referring to FIG. 1, prosthetic support pylon 10 is secured to adaptor 11 of prosthetic foot 13 by retainer 30. A second retainer 30 (not shown) can be placed on the opposite end of prosthetic support pylon 10 such that prosthetic support pylon 10 can be attached to a prosthetic lower leg, upper leg, or hip socket. Prosthetic support pylon 10 is comprised of a tubular inner member 12 and a tubular outer member 14 oriented on tubular inner member 12, as shown in the first embodiment of FIGS. 2A through 8C. Tubular inner member 12 is deformable along its longitudinal axis and is comprised of a material having a composite stiffness value of between about 30,000 pounds·inch$^2$ and about 200,000 pounds·inch$^2$. Tubular outer member 14 is comprised of a damping material which slows the release of the energy produced by tubular inner member 12 upon return from deformation along its longitudinal axis. Thus, tubular inner member 12 returns energy to the wearer's stride at "toe-off" and the damping material of tubular outer member 14 decreases the intensity of the energy produced by the tubular inner member when it recovers from longitudinal deformation following "toe-off" of the patient's stride.

Figures 2A, 2B, 3, 4, 5, 6, 7:
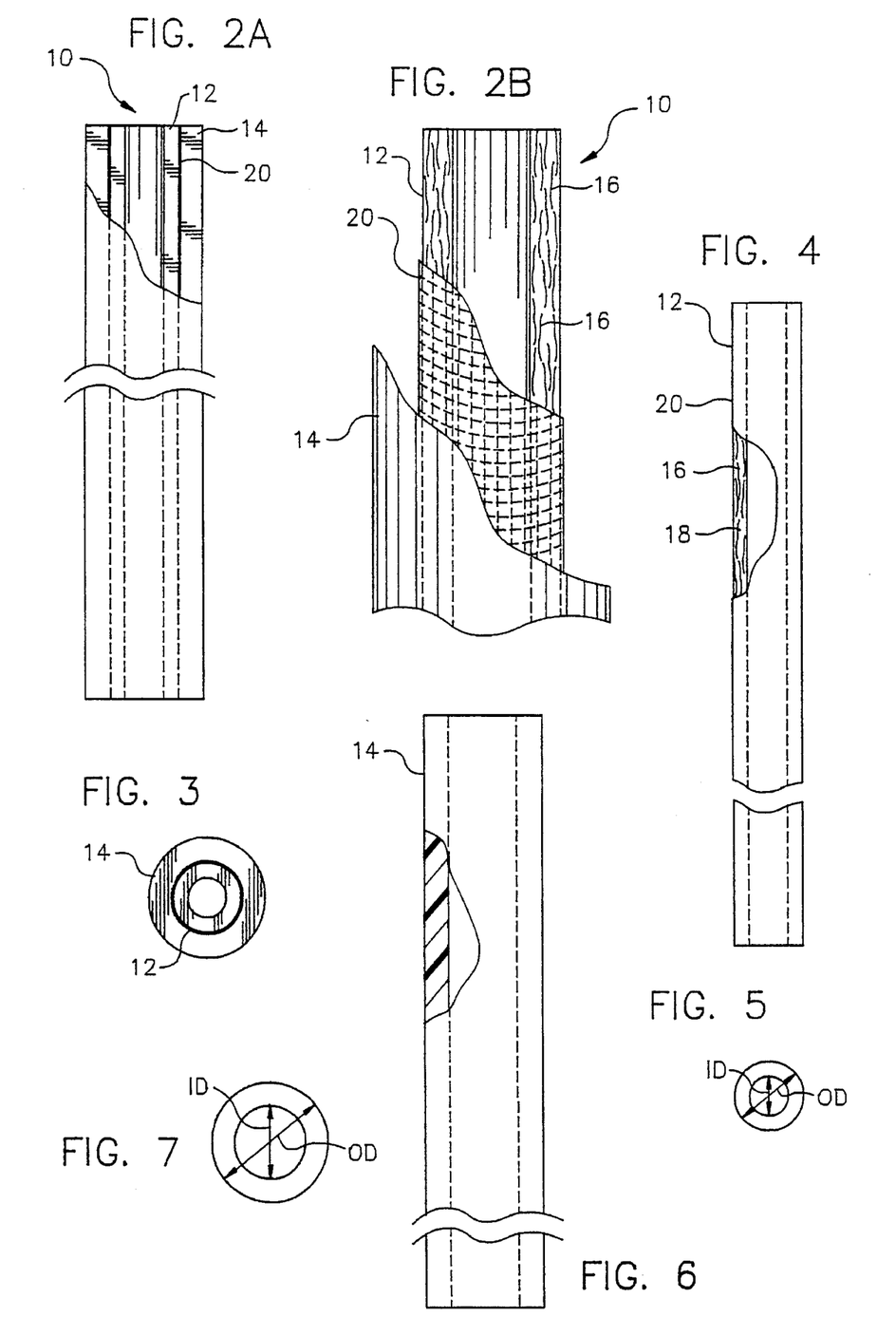
FIG. 2A is a partially exposed side view of the prosthetic support pylon of the first embodiment of the present invention.
FIG. 2B is an exposed detail view of the prosthetic support pylon of the first embodiment of the present invention.
FIG. 3 is an end view of the prosthetic support pylon of the first embodiment of the present invention.
FIG. 4 is a partially exposed side view of the tubular inner member of the prosthetic support pylon of the first embodiment of the present invention.
FIG. 5 is an end view of the tubular inner member of the prosthetic support pylon of the first embodiment of the present invention.
FIG. 6 is a partially exposed side view of the tubular outer member of the prosthetic support pylon of the first embodiment of the present invention.
FIG. 7 is an end view of the tubular outer member of the prosthetic support pylon of the first embodiment of the present invention.

Referring specifically to FIGS. 4 and 5, tubular inner member 12 is now described in detail. Tubular inner member 12 is a hollow elongate member with physical parameters and material compositions that are dictated to provide a composite stiffness of between about 30,000 pounds·inch$^2$ and about 200,000 pounds·inch$^2$. Composite stiffness is determined by the physical location of stiffening fibers employed in tubular inner member 12, the stiffness of these fibers, and the ratio of these fibers to the support matrix employed. The following physical parameters and material compositions are illustrative, but not exhaustive, of those which provide the requisite composite stiffness values. Tubular inner member 12 is preferably between about 9.50 inches and about 16.50 inches in length and has an outside diameter (O.D.) between about 0.640 inch and about 0.750 inch. When tubular inner member 12 has a length of about 9.50 inches and an outside diameter (O.D.) of about 0.640 inch, the composite stiffness is preferably between about 39,000 pounds·inch$^2$ and about 81,000 pounds·inch$^2$; when tubular inner member 12 has a length of about 9.50 inches and an outside diameter (O.D.) of about 0.750 inch, the composite stiffness is between about 150,000 pounds·inch$^2$ and about 181,000 pounds·inch$^2$; when tubular inner member 12 has a length of about 16.50 inches and an outside diameter (O.D.) of about 0.640 inch, the composite stiffness is between about 39,000 pounds·inch$^2$ and about 81,000 pounds·inch$^2$; and when tubular inner member 12 has a length of about 16.50 inches and an outside diameter (O.D.) of about 0.750 inch, the composite stiffness is between about 150,000 pounds·inch$^2$ and 181,000 pounds·inch$^2$.

The inside diameter (I.D.) is selected to produce a composite stiffness between about 30,000 pounds·inch$^2$ and about 200,000 pounds·inch$^2$ based on the above stated length and outside diameter (O.D.) requirements, and further taking into consideration the weight percent of stiffening fibers (when present) in tubular inner member 12. More specifically, as discussed below, the stiffening fibers preferably comprise about 60% by weight of tubular inner member 12.

Tubular inner member 12 is comprised of stiffening fibers 16 and a support matrix 18. Stiffening fibers 16 are preferably selected from a group consisting of carbon, graphite, fiberglass, ultra high molecular polyethylene and aramid. However, the invention is not limited to the use of the above group of materials for stiffening fibers 16. When fiberglass is employed, E, S, or RH fiberglass is most preferably used, these designations being well known in the art. When ultra high molecular weight polyethylene is employed, an ultra high molecular weight polyethylene fiber known by the trade name of "SPECTRA" is preferably employed. When aramid is used, aramid fibers known by the trade name of "KEVLAR" is preferably employed. Most preferably, carbon fibers are used as stiffening fibers 16. It is desirable, but not mandatory, to homogeneously distributed stiffening fiber 16 throughout support matrix 18 of tubular inner member 12. As stated above, stiffening fibers 16 preferably comprise about 60% by weight of tubular inner member 12. Support matrix 18 is preferably selected from the group consisting of thermoplastic and thermoset. Support matrix 18 of tubular inner member 12 most is preferably selected from the group consisting of epoxy, polyester, and vinyl ester.

Stiffening fibers 16 are preferably oriented parallel with the longitudinal axis of tubular inner member 12 in order to maximize the composite stiffness of tubular inner member 12. However, in order to prevent uncontrolled tearing of tubular inner member 12 along its longitudinal axis and in order to increase the bending stiffness, stiffening fibers 16 may also be oriented at about 45° with respect to the longitudinal axis of tubular inner member 12 such that stiffening fibers 16 are helically wound around the longitudinal axis in both clockwise and counterclockwise directions. Additionally, other orientations of stiffening fibers 16 may be employed in order to prevent tearing of tubular inner member 12.

When stiffening fibers 16 are oriented parallel with the longitudinal axis of tubular inner member 12, exterior coating 20 preferably covers tubular inner member 12, as shown in FIGS. 2B, 4 and 5. Exterior coating 20 is preferably comprised of a layer of fiberglass in an epoxy matrix. The fiberglass is comprised of fibers 21 oriented both parallel with and perpendicular to the longitudinal axis of tubular inner member 12 to add hoop strength to tubular inner member 12 in order to prevent tearing of tubular inner member 12 along its longitudinal axis.

An exemplary method of construction of tubular inner member 12 is by curing support matrix 18 (e.g. epoxy) having therein stiffening fibers 16 (e.g. carbon) and simultaneously curing exterior coating 20 (e.g. epoxy containing fiberglass). This curing can be accomplished in an autoclave in which heat and pressure is employed to activate the pre-pregnated resin (resin that is about 90% hardened) that is the precursor of the epoxy forming support matrix 18 and the epoxy in exterior coating 20. Alternatively, tubular inner member 12 can be formed by pultruding and braiding methods well known in the art.

Referring to FIGS. 6 and 7 tubular outer member 14 is described in detail. Tubular outer member 14 is a hollow elongate member having physical parameters and material compositions that are dictated to maximize the damping qualities of tubular outer member 14 such that the release of the spring back energy produced by tubular inner member 12 upon return from deformation along its longitudinal axis is slowed. Physical parameters and material compositions which are illustrative, but not exhaustive, follow. More specifically, tubular outer member 14 has a length of between about 10.00 inches and about 17.00 inches, has an inside diameter (I.D.) of between about 0.640 inch and about 0.750 inch, and has an outside diameter (O.D.) of about 1.181 inches. Preferably, tubular outer member 14 is comprised of a thermoplastic material which is most preferably selected from a group consisting of polyamide, acetal, aromatic polyester, and polysulfone. Tubular outer member 14 is most preferably made of the polyamide known as "NYLON". Tubular outer member 14 can be manufactured by either extrusion or injection molding to, or near, the final desired outside diameter and inside diameter. When tubular outer member 14 is extruded or injection molded near the final outside diameter and inside diameter, it can then be machined to the final outside diameter and inside diameter.

Figure 8A:
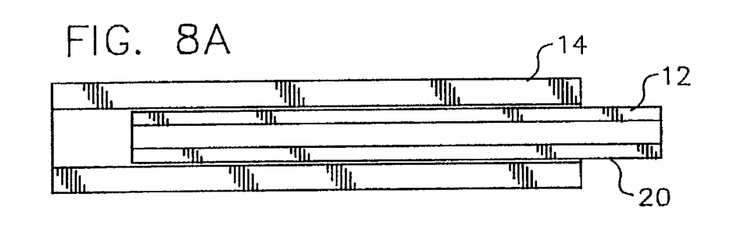
FIGS. 8A–C are cross-sectional views of an exemplary method of joining the tubular inner member and the tubular outer member of the prosthetic support pylon of the first embodiment of the present invention.
Figure 8B:
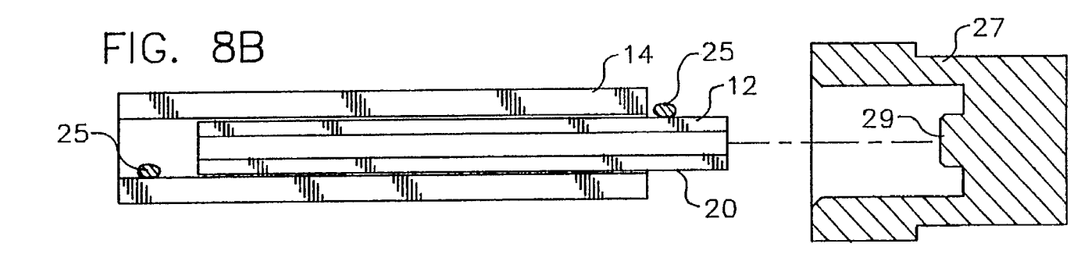
Figure 8C:
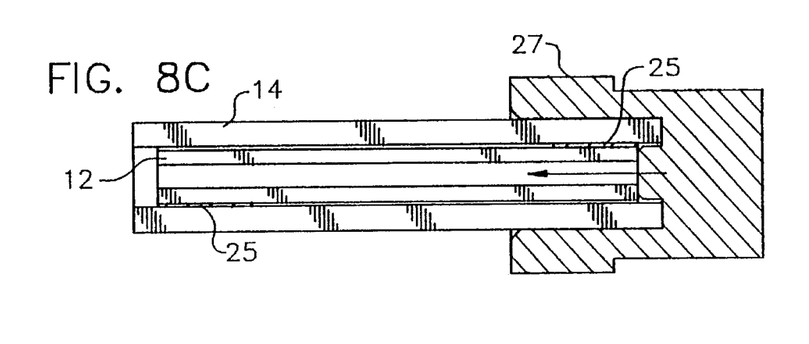

Now referring to FIGS. 8A through 8C, the attachment of tubular inner member 12 and tubular outer member 14 is described in detail. The length of tubular inner member 12 is about 0.50 inch less than that of tubular outer member 14. Preferably, the inside diameter (I.D.) of tubular outer member 14 is larger by about 0.01 inch than the outside diameter (O.D.) of tubular inner member 12 such that a gap exists when tubular inner member 12 is inserted into tubular outer member 14. As shown in FIG. 8B, after partial insertion of tubular inner member 12 into tubular outer member 14, a small portion of adhesive 25, such as cyanoacrylate, is placed on an end of the exterior surface of tubular inner member 12 and an end of the interior surface of tubular outer member 14. Thus, when tubular inner member 12 is inserted into tubular outer member 14, the cyanoacrylate adhesive 25 is evenly dispersed within a portion of the gap between tubular inner member 12 and tubular outer member 14. The relatively thin spreading of the cyanoacrylate adhesive 25 in an anaerobic environment causes the cyanoacrylate adhesive 25 to set. As shown in FIGS. 8B and 8C, jig 27 is employed to complete the insertion of tubular inner member 12 into tubular outer member 14 such that the formed prosthetic support pylon 10 has two ends of about 0.25 inch each that lack tubular inner member 12. These ends can be removed when prosthetic support pylon 10 is eventually cut to size. The above placement of tubular inner member 12 within tubular outer member 14 is accomplished by seat 29 of jig 27, which is a raised, circular portion of the interior bottom of jig 27 having a height of about 0.25 inch and a diameter about equal to the outside diameter (O.D.) of tubular inner member 12 but less than the inside diameter (I.D.) of tubular inner member 14.

Figure 9:
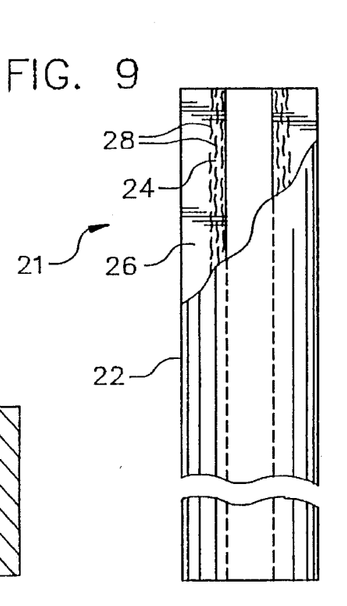
FIG. 9 is a partially exposed side view of the unitary tubular member of the prosthetic support pylon of the second embodiment of the present invention.
Figure 10:
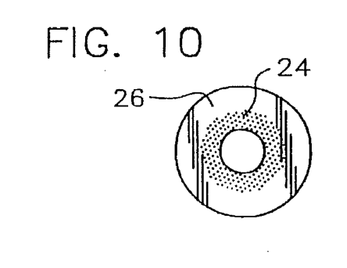
FIG. 10 is an end view of the unitary tubular member of the prosthetic support pylon of the second embodiment of the present invention.

Referring to FIGS. 9 and 10, a second embodiment of the prosthetic support pylon of the present invention is described in detail. In this embodiment of the present invention, prosthetic support pylon 21 is comprised of a unitary tubular member 22 consisting of a tubular inner portion 24 and a tubular outer portion 26. It is important to note that, unlike the first embodiment of the present invention where tubular inner member 12 and tubular outer member 14 are separate components bound with an adhesive, tubular inner portion 24 and tubular outer portion 26 are two different layers of a structurally integral, monolithic unitary tubular member 22. The values for length, outside diameter (O.D.), inside diameter (I.D.) and composite stiffness of the first embodiment of the present invention are incorporated by reference into the present description of the second embodiment. Both tubular inner portion 24 and tubular outer portion 26 of unitary tubular member 22 are preferably comprised of a material selected from the group consisting of thermoplastic and thermoset. Most preferably, polyamide, vinyl ester, or acetal are employed. These materials provide the damping qualities necessary for tubular outer portion 26 which were more fully described in respect to tubular outer member 14 of the first embodiment of the present invention.

Additionally, tubular inner portion 24 is further comprised of stiffening fibers 28 preferably selected from a group consisting of carbon, graphite, fiberglass, ultra high molecular weight polyethylene and aramid, as described in more detail with respect to stiffening fibers 16 of the first embodiment of the present invention. Again, the invention is not limited to the use of the above group of materials for stiffening fibers 28. It is important to note that stiffening fibers 28 are only present in tubular inner portion 24 and do not exceed the outside diameter (O.D.) thereof. In contrast to the first embodiment of the present invention, prosthetic support pylon 21 of the second embodiment does not necessarily require an exterior coating 20 comprised of fiberglass and epoxy in order to prevent tearing of tubular inner portion 24 along its longitudinal axis because of the unitary construction of prosthetic support pylon 21 in which tubular outer portion 26 supports tubular inner portion 24.

Prosthetic support pylon 21 of the second embodiment of the present invention can be manufactured by a pultrusion, extrusion, compression molding, or injection molding techniques well known in the art.

Figure 11A:
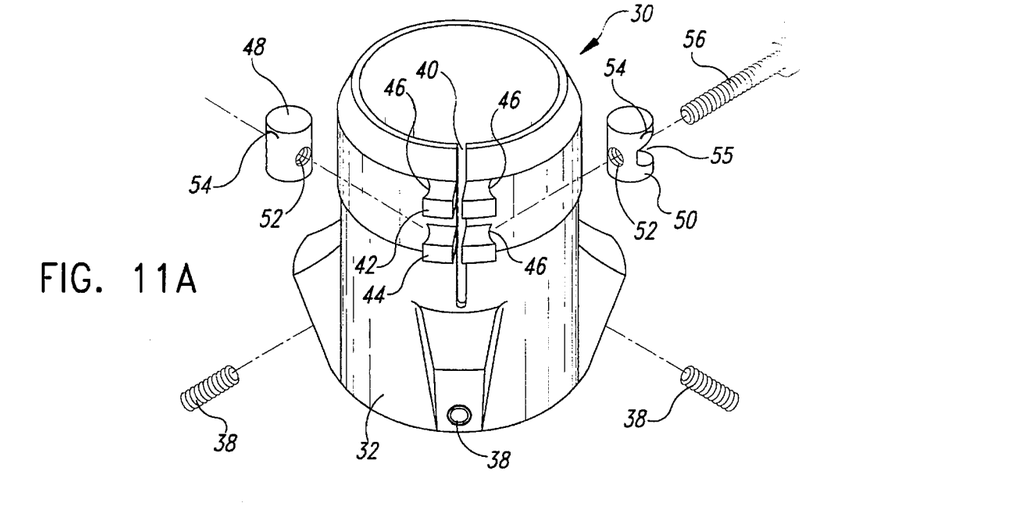
FIG. 11A is an isometric view of the retainer of the prosthetic support pylon retainer of the present invention oriented in a first position to receive a polymeric prosthetic support pylon.
Figure 11B:
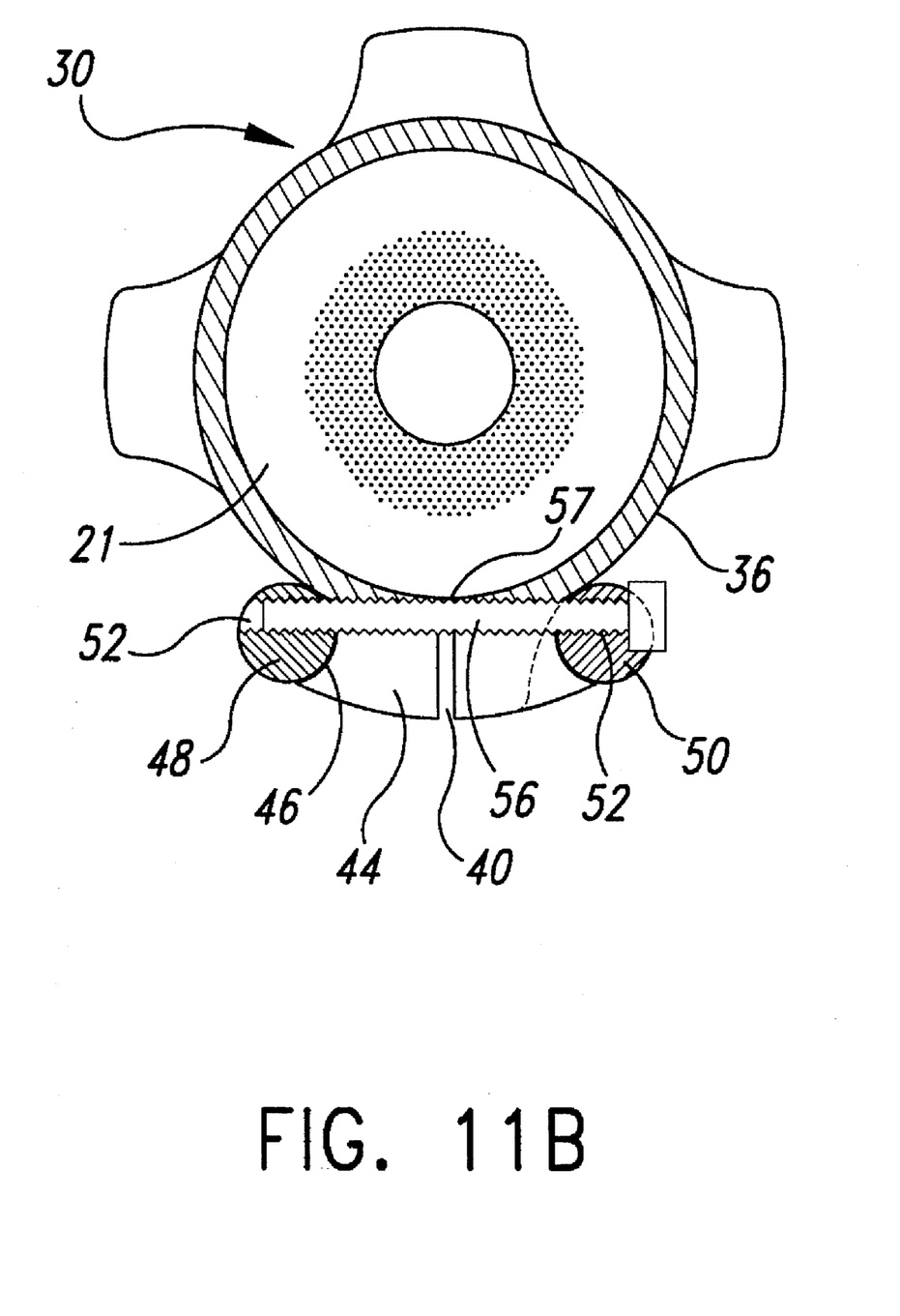
FIG. 11B is a top view of the retainer of FIG. 11A holding a polymeric prosthetic support pylon.
Figures 12A, 12B:
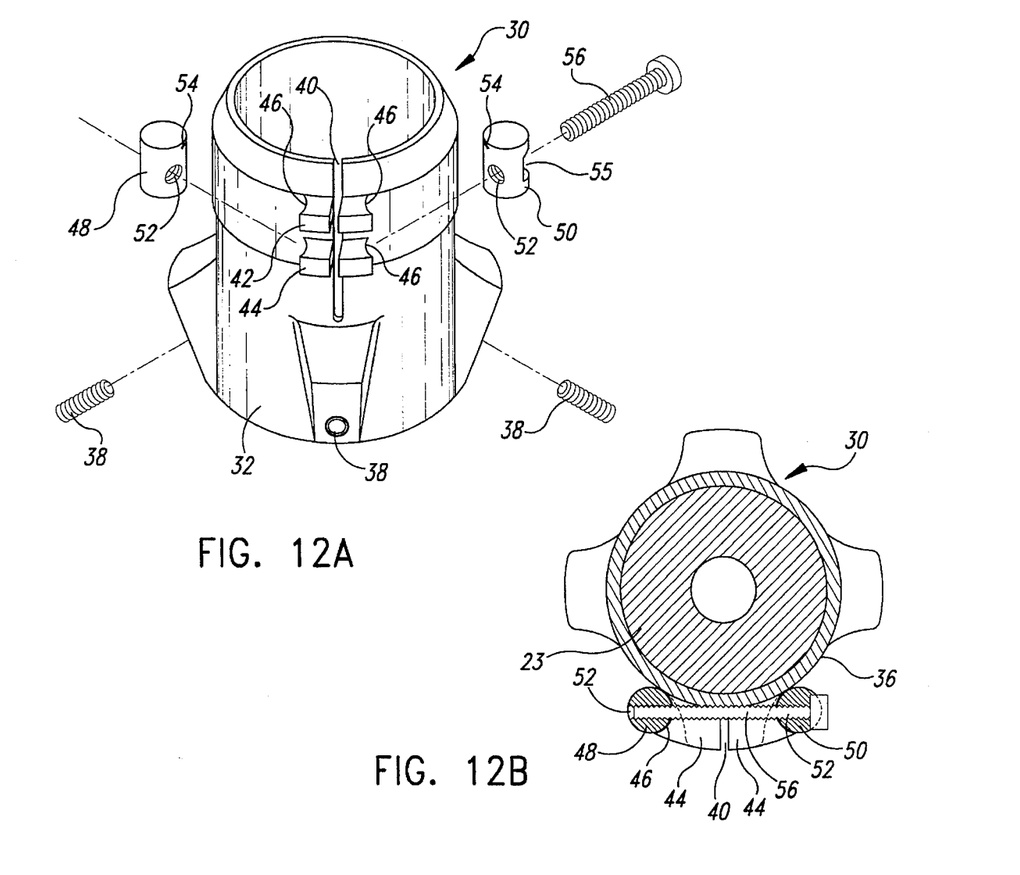
FIG. 12A is an isometric view of the prosthetic support pylon retainer of the present invention oriented in a second position to receive an alloy prosthetic support pylon.
FIG. 12B is a top view of FIG. 12A holding an alloy prosthetic support pylon.
Figure 13:
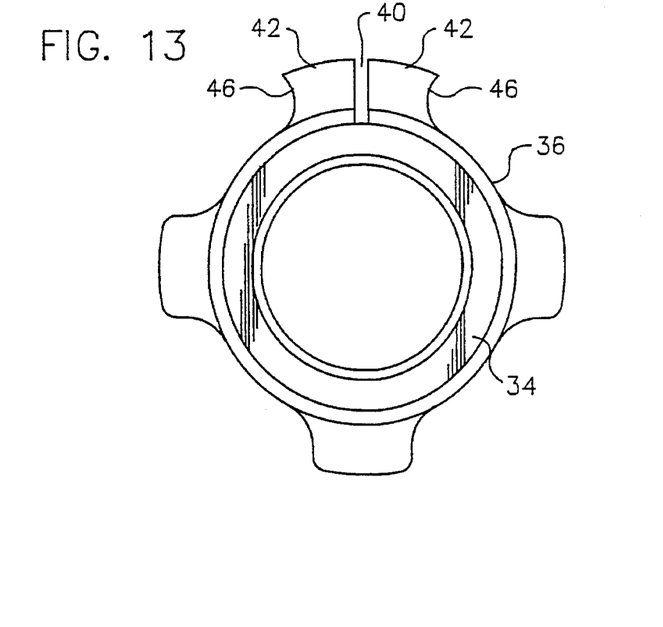
FIG. 13 is a top view of the prosthetic support pylon retainer of the present invention.

Referring now to FIGS. 11 through 13, prosthetic support pylon retainer 30 is described in detail. Retainer 30 is comprised of a sleeve 32 having a bottom 34, and a wall 36 circumferentially disposed around bottom 34 such that the end of a prosthetic support pylon 10 or 21 can be held in retainer 30. Bottom 34 includes an opening through which the shaft of a prosthetic foot (not shown) can be inserted and tightened in place with set screws 38. Wall 36 has a longitudinally disposed opening, or slot 40, therein. Slot 40 bisects a pair of flanges 42 and 44 which are oriented in tandem longitudinally along a portion of wall 36 of retainer 30. Flange 42 and flange 44 each have a pair of barrel nut seats 46, with one barrel nut seat 46 located at each end of flange 42 and at each end of flange 44. Thus, two barrel nut seats 46 are adapted to receive barrel nut 48 and two barrel nut seats 46 are adapted to receive barrel nut 50. Barrel nut 48 and barrel nut 50 both have a screw hole 52 passing therethrough perpendicular to their respective longitudinal axis and oriented off-center with respect to their respective longitudinal axis. Barrel nut 48 and barrel nut 50 also each have a groove 54 on a side thereof. Groove 54 is employed as a point of reference from which one can readily ascertain the axial orientation of barrel nut 48 and barrel nut 50 with respect to retainer 30. Barrel nut 50 also includes an opening 55 in a side thereof through which screw 56 can be inserted. Barrel nut 48 and barrel nut 50 are held in seats 46 of flange 42 and 44 when screw 56 is placed through screw holes 52 such that screw 56 passes between flange 42 and flange 44. The longitudinal axis of screw 56 is thus substantially perpendicular to the length of slot 40 and to the longitudinal axis of a prosthetic support pylon within retainer 30.

Referring specifically to FIGS. 11A and 11B, when barrel nut 48 and barrel nut 50 are configured in a first position such that grooves 54 are facing outwardly from wall 36 of retainer 30, screw holes 52 are aligned such that the threads of screw 56 protrude through slot 40 and into retainer 30. In this interference-fit configuration, the threads of screw 56 bite into the exterior surface of a prosthetic support pylon comprised of a synthetic polymer, such as prosthetic support pylon 10 of the first embodiment of the present invention or prosthetic support pylon 21 of the second embodiment of the second invention, thus preventing axial rotation of the prosthetic support pylon 10 or 21 with respect to retainer 30. More specifically, the threads of screw 56 initially create self-made thread marks on the pylon's soft polymeric exterior, and then as sleeve 32 tightens, the threads of screw 56 shear away polymeric material to form a slight semi-circumferential groove 57 in the pylon. This groove 57 is tangent to the circumference of support pylon 10 or 21. Due to its viscous qualities, the synthetic polymeric material of pylon 10 or 21 within the sheared groove 57 then creeps into the spacings between the threads of screw 56 to embed the thread extremities into the pylon material, further securing screw 56 and sleeve 32 to support pylon 10 or 21.

Now referring to FIGS. 12A and 12B, axial rotation of barrel nut 48 and barrel nut 50 such that grooves 54 are oriented inwardly toward wall 36 of retainer 30 configures screw holes 52 of barrel nut 48 and barrel nut 50 in a second orientation such that the threads of screw 56 do not protrude through slot 40 into retainer 30. Thus, in contrast to FIG. 11 in which an interference fit of screw 56 and retainer 30 was shown, FIG. 12 shows a clearance fit between screw 56 and retainer 30 that is employed with a prosthetic support pylon 23 comprised of an alloy into which the threads of screw 56 cannot bite.

While particular embodiments of the present invention have been described in some detail hereinabove, changes and modifications may be made in the illustrated embodiments without departing from the spirit of the invention.

What is claimed is:

1. A prosthetic support pylon comprising:

a tubular inner member being deformable along its longitudinal axis and comprised of a material having a composite stiffness value of between about 39,000 pounds per square inch and about 181,000 pounds per square inch; and a tubular outer member coaxially surrounding said tubular inner member, said tubular outer member comprised of a material having a damping coefficient that is greater than the damping coefficient of the material forming the inner member, the ends of the tubular outer member being mechanically coupled to the adjacent ends of the tubular inner member so that the inner and outer tubular members expand and contract with each other whereby the outer member decreases the intensity of the energy produced by said tubular inner member upon return from a deformation along its longitudinal axis.

2. The prosthetic support pylon of claim 1 wherein said tubular inner member material is comprised of a support matrix and of fibers selected from a group consisting of carbon, graphite, fiberglass, ultra high molecular weight polyethylene, and aramid.

3. The prosthetic support pylon of claim 2 wherein said support matrix is selected from the group consisting of epoxy, polyester, and vinyl ester.

4. The prosthetic support pylon of claim 2 wherein said fibers are homogeneously distributed in said support matrix.

5. The prosthetic support pylon of claim 2 wherein said fibers are oriented parallel with the longitudinal axis of said tubular inner member.

6. The prosthetic support pylon of claim 2 wherein said fibers are oriented at about 45° with respect to the longitudinal axis of said tubular inner member and which are helically wound around the longitudinal axis of said tubular inner member in both clockwise and counter clockwise directions.

7. The prosthetic support pylon of claim 2 wherein said fibers comprise about 60 percent by weight of said tubular inner member.

8. The prosthetic support pylon of claim 1 wherein said tubular inner member is comprised of carbon fibers in a support matrix.

9. The prosthetic support pylon of claim 1 wherein the composite stiffness value of said tubular inner member is between about 39,000 pounds per square inch and about 81,000 pounds per square inch.

10. The prosthetic support pylon of claim 1 wherein the composite stiffness value of said tubular inner member is between about 150,000 pounds per square inch and about 181,000 pounds per square inch.

11. The prosthetic support pylon of claim 1 wherein said tubular inner member further comprises a layer of fiberglass in an epoxy matrix on the exterior surface of said tubular inner member.

12. The prosthetic support pylon of claim 11 wherein said fiberglass is comprised of fibers oriented parallel with and perpendicular to the longitudinal axis of said tubular inner member.

13. The prosthetic support pylon of claim 1 wherein said pylon has a length of between about 10 inches and about 17 inches, said tubular inner member has an outside diameter of between about 0.640 inch and about 0.750 inch, and said tubular outer member has an inside diameter of between about 0.640 inch and about 0.750 inch.

14. The prosthetic support pylon of claim 1 wherein said tubular outer member material is selected from a group consisting of polyamide, acetal, aromatic polyester, and polysulfone.

15. The prosthetic support pylon of claim 1 wherein the adjacent ends of said tubular inner and outer members are mechanically coupled to each other by respective layers of adhesive positioned therebetween.

\* \* \* \* \*